United States Patent [19]
Ueda

[11] 4,439,030
[45] Mar. 27, 1984

[54] CONNECTING DEVICE FOR AN ENDOSCOPIC TELEVISION CAMERA

[75] Inventor: Yasuhiro Ueda, Tokyo, Japan

[73] Assignee: Olympus Optical Co., Ltd., Tokyo, Japan

[21] Appl. No.: 420,235

[22] Filed: Sep. 20, 1982

[30] Foreign Application Priority Data

Oct. 12, 1981 [JP] Japan .............................. 56-162202

[51] Int. Cl.³ .................... A61B 1/04; G03B 29/00
[52] U.S. Cl. .................................... 354/62; 128/4; 358/98
[58] Field of Search ............... 354/62, 63, 79, 223; 358/98; 128/4, 6

[56] References Cited

U.S. PATENT DOCUMENTS 2,280,561 4/1942 Wappler ............................ 354/62
4,192,591 3/1980 Yobaccio .......................... 354/62

FOREIGN PATENT DOCUMENTS 2851251 6/1980 Fed. Rep. of Germany .
56-80102 6/1981 Japan .
56-151018 11/1981 Japan .

Primary Examiner—John Gonzales

[57] ABSTRACT

A connecting device for optically and mechanically connecting an eyepiece section of an endoscope and a light receiving section of a television camera so that the optical axes of these sections are in alignment comprises a cylindrical housing having one end connectable to the eyepiece section and the other end connectable to the light receiving section, a prism located between the eyepiece section and the light receiving section, and having a first optical axis in alignment with the optical axis extending from the eyepiece section to the light receiving section, and a second optical axis at right angles to the first optical axis, a holder in the housing for supporting the prism so as to be able to rock relative to the housing around the first optical axis, a finder extension tube for the connecting device connected to the holder so as to be rockable therewith and extending outward from the peripheral surface of the housing along the second optical axis for observation of an endoscopic picture, and a click mechanism capable of fixing the holder in a predetermined position.

8 Claims, 8 Drawing Figures

CONNECTING DEVICE FOR AN ENDOSCOPIC TELEVISION CAMERA

BACKGROUND OF THE INVENTION

This invention relates to a connecting device for an endoscopic television camera provided with an eyepiece section for the connecting device connecting an eyepiece section of an endoscope and the television camera, whereby televising and endoscopic observation can be performed simultaneously.

Generally known is a televising technique where an endoscopic television camera is connected to an eyepiece section of an endoscope to project a picture on a television monitor. Since the picture provided by the endoscopic television camera is subject to imperfect color reproduction, it is necessary to observe a direct endoscopic picture. To do this, there is developed a system (e.g., U.S. Pat. No. 4,192,591) in which a connecting device connecting the eyepiece section of the endoscope and the television camera is provided with a finder so that endoscopic observation can be made simultaneously with televising. In this case, the finder and the television camera are located on and off the optical axis of the eyepiece section of the endoscope, respectively. During operation, therefore, the weight of the endoscope is ill balanced resulting in poor operating efficiency.

SUMMARY OF THE INVENTION

This invention is contrived in consideration of these circumstances, and is intended to provide a connecting device for an endoscopic television camera, provided with an eyepiece section for the connecting device which is rockable around an optical axis connecting an endoscope and a television camera unit, thereby maintaining weight balance and improving operating efficiency.

BRIEF DESCRIPTION OF THE DRAWINGS

FIGS. 1 to 7 show a connecting device according to one embodiment of this invention, in which;

FIG. 1 is a general perspective view showing an endoscope and a television camera assembly connected with each other, FIG. 2 is a partial plan view of the connecting device, FIGS. 3 to 5 are sectional views taken along line A-B-C of FIG. 2, showing different operating states, and FIGS. 6 and 7 are partial perspective views showing a rocking guide opening of a housing and a finder extension tube in different operating positions.

DETAILED DESCRIPTION OF THE PREFERRED EMBODIMENTS

Figure 1:
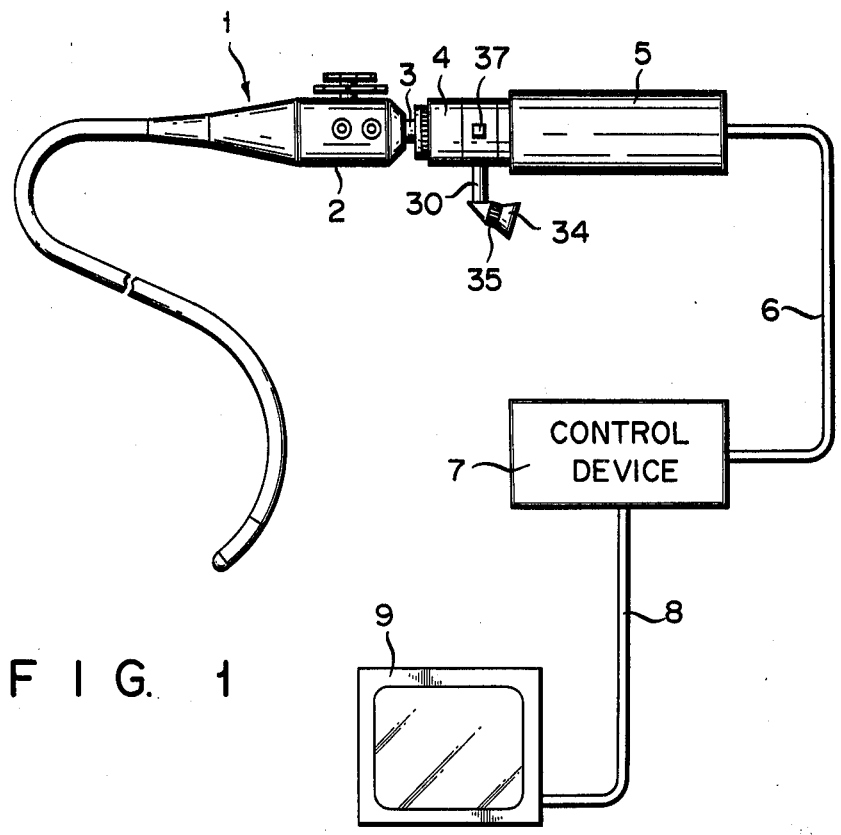
Figure 2:
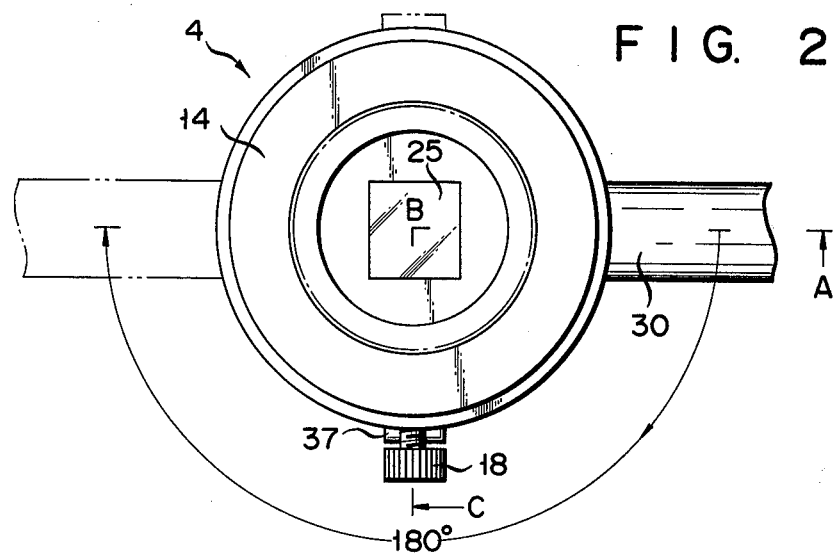

There will now be described one embodiment of this invention with reference to the accompanying drawings. Referring first to the general view of FIG. 1, numeral 1 designates an endoscope. An operating section 2 of the endoscope 1 is provided with an eyepiece section 3 with an eyepiece built-in. The eyepiece section 3 is mechanically and optically connected with a television camera unit 5 by means of a connecting device 4. The television camera unit 5 is connected to a television camera control device 7 by means of a cable 6. At the television camera control device 7, an electric signal delivered from the television camera unit 5 is amplified and converted into a video signal, and a synchronizing signal is produced and added to the video signal to provide a composite video signal. The television camera control device 7 is connected to a television monitor 9 by means of a cable 8 so that a composite video signal is delivered to the television monitor 9 to appear as a picture thereon.

Referring then to FIGS. 2 to 7, there will be described in detail the connecting device 4 and the television camera unit 5. Numeral 10 designates a pickup tube which has both a light-electricity converting function and a scanning function, and is provided at one end with an image pickup surface 11. The pickup tube 10 is coaxially held in a cylindrical camera housing 12. A connecting port 13 is formed in the end wall of the camera housing 12 on the same side as the image pickup surface 11. An internal thread to mate with a screw mount 14 of the connecting device 4 is formed on the peripheral surface of the connecting port 13. The screw mount 14 is fixed to a mount clamping portion 15 by means of screws 16, and the mount clamping portion 15 is fitted with a fixing screw 18 for fixing it to a housing 17. The housing 17 is cylindrical, and a fixing ring 19 is fixed by means of a screw 20 to that end face of the housing 17 which is opposed to the television camera unit 5. An inner cylinder 21 fitted on the eyepiece section 3 of the endoscope 1 is coaxially attached to the inner peripheral surface of the housing 17 on the side of the endoscope 1. That portion of the housing 17 which faces the television camera unit 5 is somewhat narrowed to form a small-diameter portion 22 on which an outer cylinder 23 is fitted so as to be able to rotate about its central axis. Disposed in the housing 17 is a cylindrical prism holder 24, which can rock around a first optical axis $O_1$ of the endoscope 1 and the pickup tube 10. A prism 25 and a lens 26 are arranged on the first optical axis $O_1$ of the prism holder 24. The lens 26 is fixed to a cylindrical lens frame 27, which is coaxially screwed in the prism holder 24. The tip end portions of retaining screws 28 vertically penetrating the lens frame 27 abut against the prism holder 24 to locate the lens frame 27 in position along the optical axis $O_1$. A penetrating hole 29 extending at right angles to the first optical axis $O_1$ is bored through the peripheral wall of the prism holder 24 which optically faces the prism 25. The proximal end portion of a finder extending section, e.g., a finder extension tube 30, is screwed in the penetrating hole 29. The finder extension tube 30 projects sideways through a rocking guide opening 31 bored through the housing 17 over an angle of 270° along its circumference and a mounting hole 32 bored through the outer cylinder 23. Thus, the outer cylinder 23 and the prism 24 can rock together over 180° around the first optical axis $O_1$. Arranged in the finder extension tube 30 is an optical system 33 composed of a lens or the like to form a second optical axis $O_2$ which extends at right angles to the first optical axis $O_1$. The distal end portion of the finder extension tube 30 is fitted with an eyepiece section 34 for the connecting device 4 which extends substantially parallel to the television camera unit 5. A visibility adjusting ring 35 is attached to the eyepiece section 34 for the connecting device 4. In this embodiment, the distance l between the respective axes of the eyepiece section 34 and the connecting device 4 is 60 mm to 70 mm. This length is the shortest optimum length determined in consideration of the size of the face of a person who looks into the eyepiece section 34 with his right eye. In other words, the connecting device 4 is minimized in size. A recess portion 36 is formed in the outer peripheral surface of the prism holder 24 in a position at an angular distance of 90° from the finder extension tube 30. Disposed in the recess portion 36 is a retaining button 37 which can project and be depressed radially. The retaining button 37 is urged outward by the restoring force of a coil spring 38 interposed between the bottom of the retaining button 37 and the bottom of the recess portion 36, and is fitted with a retaining click 39 on the back. The retaining button 37 penetrates the rocking guide opening 31 of the housing 17 to project outward through an opening 40 bored through the outer cylinder 23. The retaining click 39 forms a click mechanism 41 which engages indentations 41a and 41b (FIGS. 6 and 7) in the lower edge of the rocking guide opening 31 to restrain the rocking motion of the prism holder 24. The engaging indentations 41a and 41b are located in the center of the maximum rocking range (180°) of the finder extension tube 30 and in the position at an angular angle of 180° from the center, respectively. Namely, the one engaging indentation 41b is formed at the end of the guide opening 31, while the other engaging indentation 41a is at an angular distance of 180° from the end. Thus, if the finder extension tube 30 is rocked around the first optical axis $O_1$ to be located at one or the other end of its maximum rocking range, the retaining click 39 will engage the engaging indentation 41a or 41b to hold the prism 24 fixedly.

Figure 3:
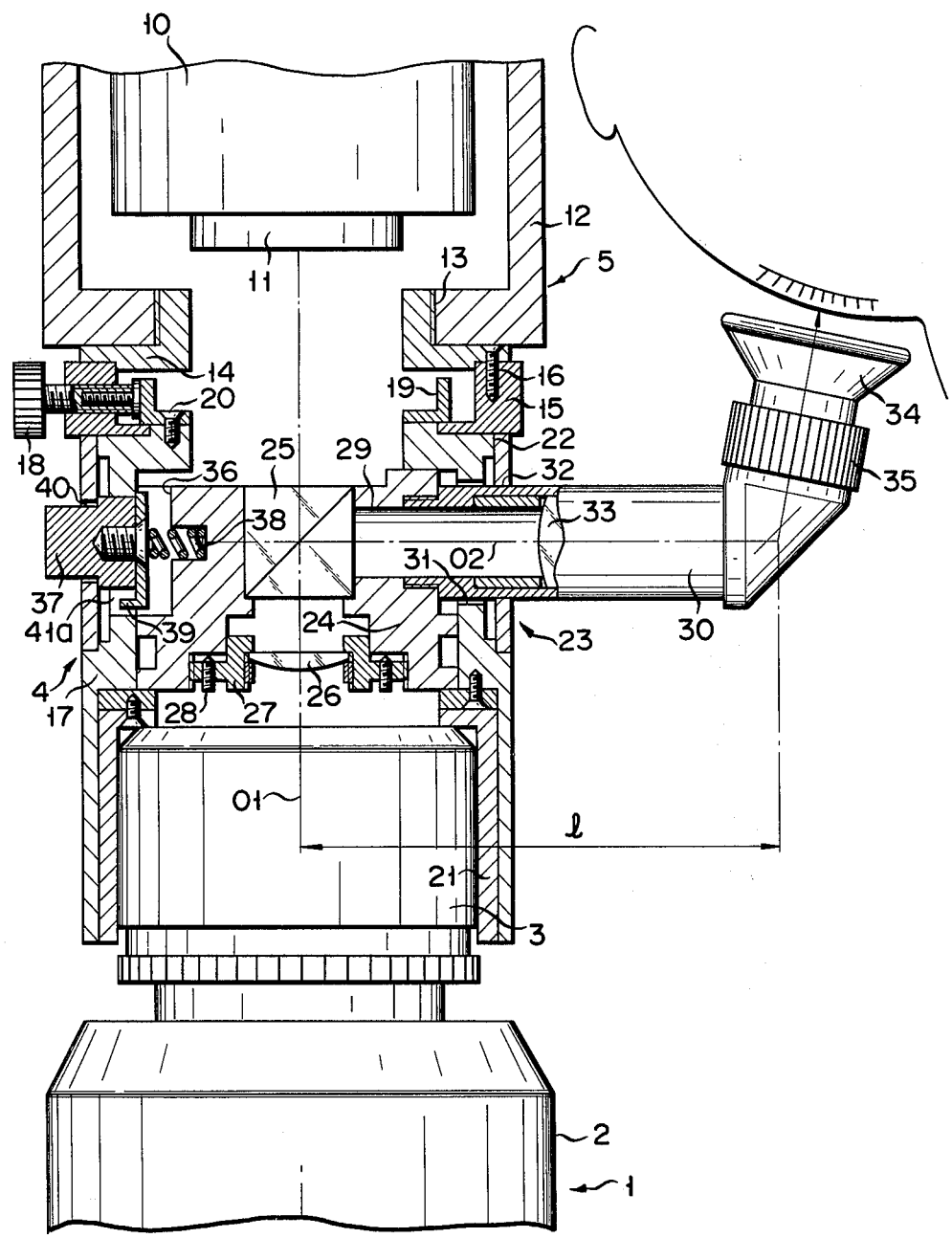

There will now be described the operation of the connecting device for an endoscopic television camera of the aforementioned construction. In directly observing an endoscopic picture through the endoscope 1 while conducting television shooting, an observer may use his right or left eye. When observing with the right eye, the observer rocks the eyepiece section 34 for the connecting device 4 to the left facing the endoscope mounting side, as shown in FIG. 3. At this time, if the finder extension tube 30 is rocked relative to the housing 17 of the connecting device 4 in the direction indicated by the arrow of FIG. 7 along the rocking guide opening 31, the prism holder 24 rocks around the first optical axis $O_1$, and the retaining button 37 moves in the same direction. When the finder extension tube 30 reaches a predetermined position, that is, the one end of the rocking guide opening 31, the retaining click 39 of the retaining button 37 urged by the coil spring 38 engages the engaging indentation 41$_a$. Accordingly, the prism holder 24 is kept fixed to the housing 17, so that the finder extension tube 30 integral with the prism holder 24 is also fixed to the housing 17, and will never be moved by the eyepiece section 34 during observation.

Figure 4:
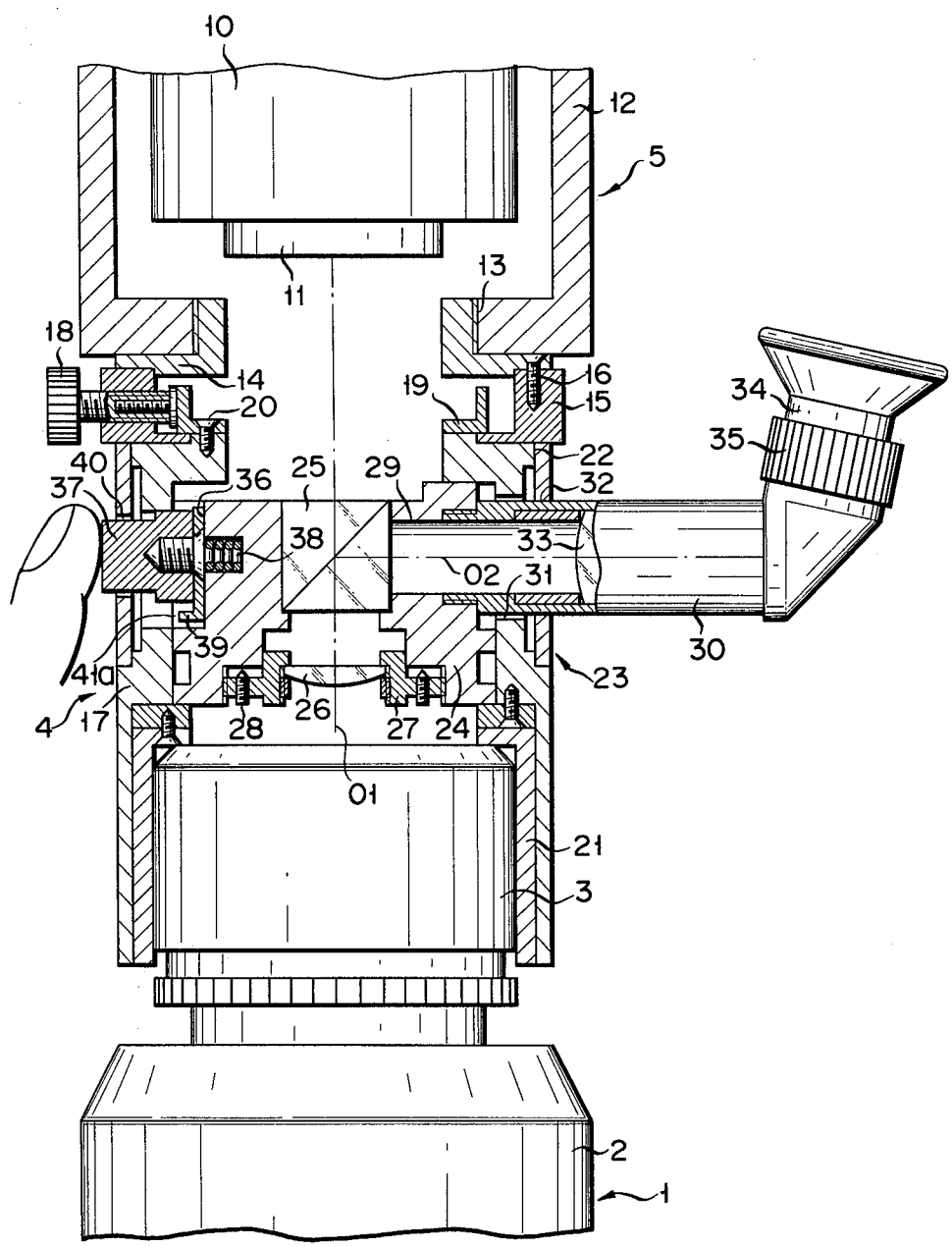
Figure 5:
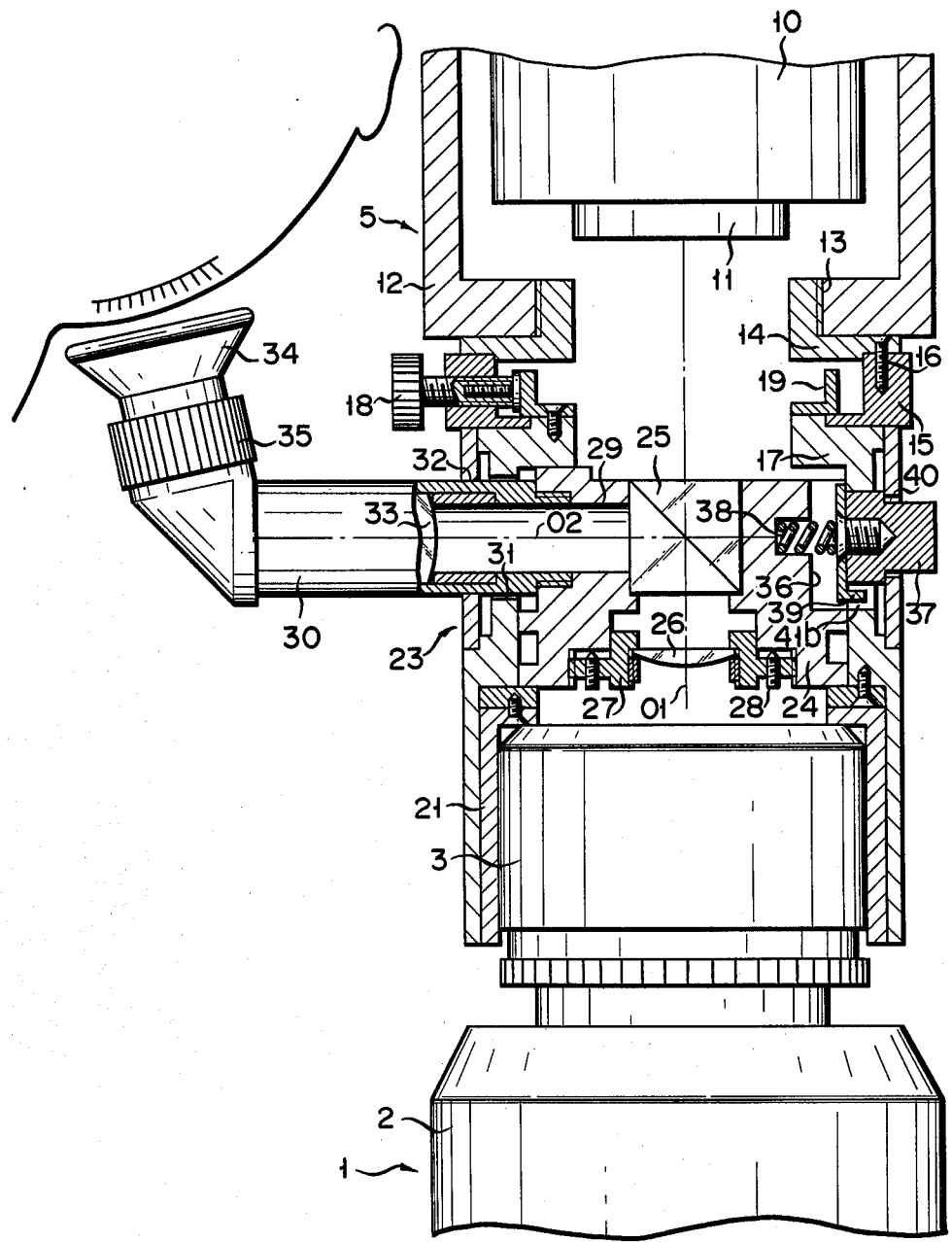
Figure 6:
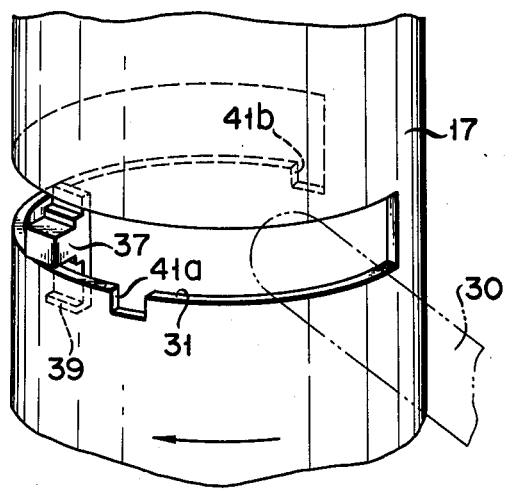
Figure 7:
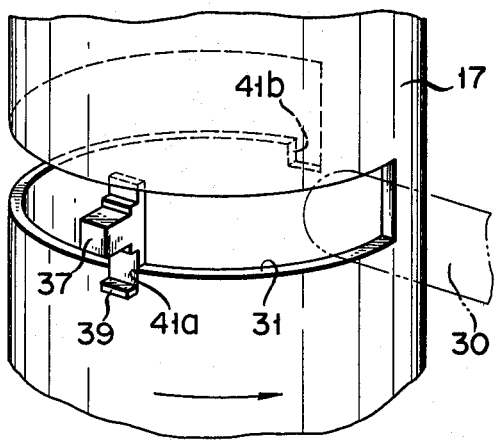

When observing with the left eye, the observer first pushes in the retaining button 37 against the restoring force of the coil spring 38 with his finger to disengage the retaining click 39 from the engaging indentation 41a, as shown in FIG. 4. In this state, if the finder extension tube 30 is rocked relative to the housing 17 in the direction indicated by the arrow of FIG. 6, it rocks along the rocking guide opening 31, and the retaining click 39 slides along the inner peripheral surface of the housing 17. When the rocking angle covered by the finder extension tube 30 reaches 180°, that is, when the tube 30 is located on the right side as viewed from the endoscope mounting side, the retaining click 39 engages the engaging indentation 41b. Accordingly, the prism holder 24 and hence the finder extension tube 30 integral therewith are fixed to the housing 17.

Thus, the eyepiece section 34 for the connecting device 4 can rock through 180° relative to the housing 17, so that the observer may observe with his right or left eye by preference.

Figure 8:
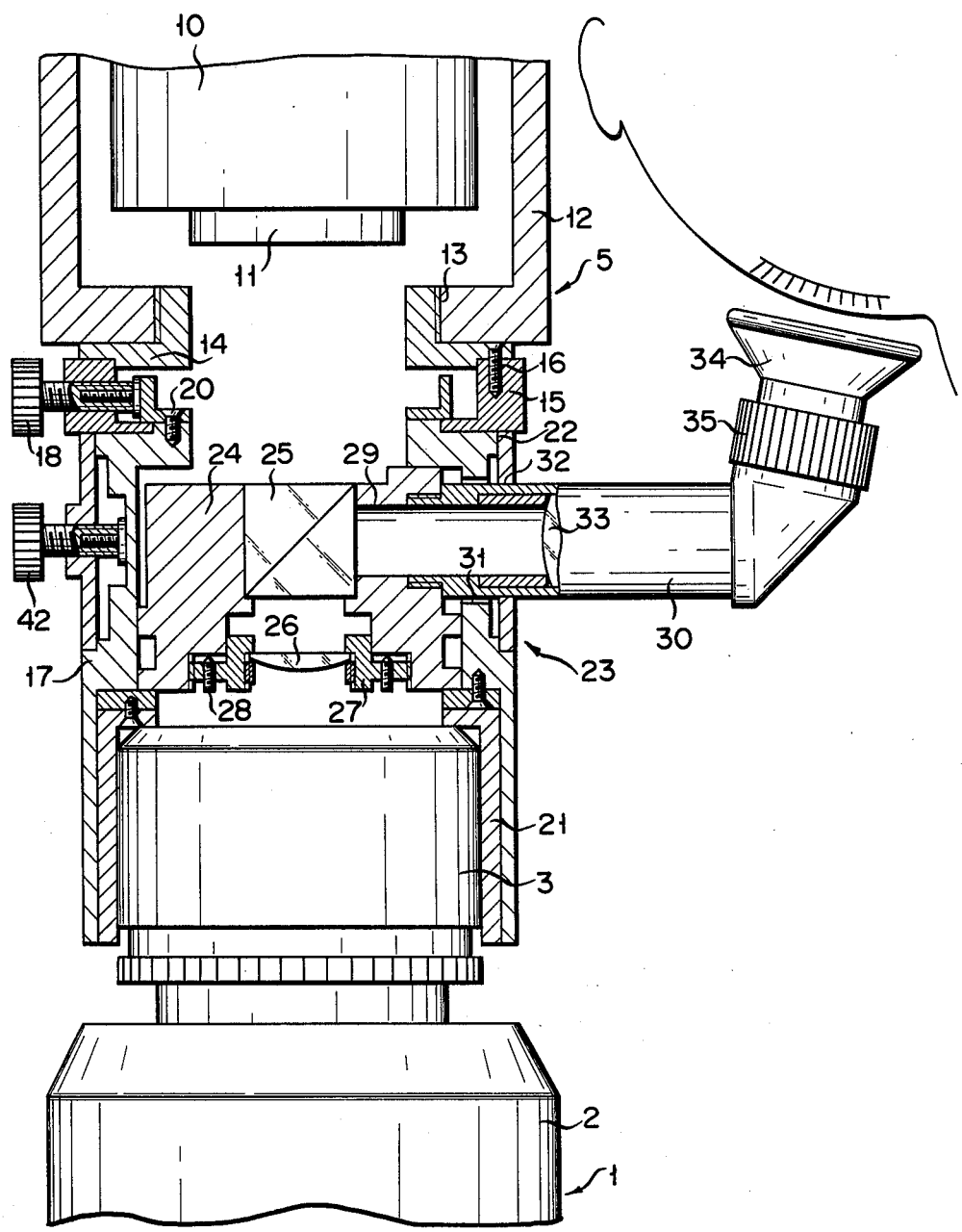
FIG. 8 is a sectional view similar to FIG. 3 showing a connecting device according to another embodiment.

In the aforementioned embodiment, the eyepiece section 34 for the connecting device 4 is fixed through the engagement between the retaining click 39 attached to the retaining button 37 and the engaging indentations 41a and 41b formed in the rocking guide opening 31. Alternatively, however, the rockable outer cylinder 23 may be fitted with a retaining screw 42 so that the eyepiece section 34 for the connecting device 4 is fixed in position by frictional force produced when the retaining screw 42 is screwed into the outer cylinder 23 to have its tip end pressed against the outer side wall of the housing 17, as shown in FIG. 8. In FIG. 8, like reference numerals are used to designate the same components as included in the foregoing embodiment.

In the connecting device of the invention connecting an endoscope and a television camera unit, as described above, a finder extending section having a second optical axis is located at right angles to a first optical axis connecting the endoscope and a pickup tube of the television camera unit, and an eyepiece section for the connecting device for observation of an endoscopic picture is attached to the finder extending section. In this device, moreover, the finder extending section can rock around the first optical axis and be fixed in a predetermined position or positions. Thus, the endoscope and the television camera unit are made coaxial, so that the endoscope is well balanced in weight. In observation, furthermore, an observer may use his right or left eye, and the operating efficiency is improved.

What is claimed is:

1. A connecting device for optically and mechanically connecting an eyepiece section of an endoscope and a light receiving section of a television camera so that the optical axes of these sections are in alignment, comprising:
   a cylindrical housing having one end connectable to the eyepiece section and the other end connectable to the light receiving section;
   a finder extending section located between the eyepiece section and the light receiving section, and having a first optical axis in alignment with the optical axis extending from the eyepiece section to the light receiving section, and a second optical axis at a given angle to the first optical axis;
   supporting means in the housing for supporting the finder extending section so as to be able to rock relative to the housing around the first optical axis;
   an eyepiece section for the connecting device connected to the supporting means so as to be rockable therewith and extending outward from the peripheral surface of the housing along the second optical axis for observation of an endoscopic picture through the eyepiece section of the endoscope; and
   fixing means capable of fixing the supporting means in a predetermined position.

2. The connecting device according to claim 1, wherein said second optical axis intersects the first optical axis at right angles, and said eyepiece section extends radially from the housing.

3. The connecting device according to claim 2, wherein said eyepiece section includes a bent portion at the extended end thereof extending in the same direction as the television camera, and an eyepiece section attached to the bent portion.

4. The connecting device according to claim 3, wherein said supporting means can rotate the finder extending section through 180°.

5. The connecting device according to claim 4, wherein said fixing means fixes the supporting means in two positions at an angular distance of 180°.

6. The connecting device according to claim 5, wherein said supporting means includes a cylindrical holder coaxially disposed in the housing to hold the finder extending section and rockable around the first optical axis, and an outer cylinder coaxially fitted on the outer periphery of the housing and connected to the cylindrical holder so as to be rockable therewith.

7. The connecting device according to claim 6, wherein said fixing means includes a click mechanism disposed between the supporting means and the housing.

8. The connecting device according to claim 4, wherein said fixing means fixes the supporting means to any position.

* * * * *